United States Patent [19]

Hartman

[11] 4,414,215

[45] Nov. 8, 1983

[54] N-ACYL DERIVATIVES OF 6-ALKYLAMINO 5-CHLORO-3-NITROPYRAZINAMINES FOR RADIATION THERAPY

[75] Inventor: George D. Hartman, Lansdale, Pa.

[73] Assignee: Merck & Co., Inc., Rahway, N.J.

[21] Appl. No.: 399,382

[22] Filed: Jul. 19, 1982

Related U.S. Application Data

[63] Continuation-in-part of Ser. No. 295,445, Aug. 24, 1981, abandoned, which is a continuation-in-part of Ser. No. 194,092, Oct. 6, 1980, abandoned.

[51] Int. Cl.$^3$ .................. A61K 31/495; C07D 241/16; C07D 241/20
[52] U.S. Cl. .................................... 424/250; 544/120; 544/359; 544/409; 414/248.4
[58] Field of Search ............... 544/409, 120, 359, 405; 424/250, 248.4

[56] References Cited

U.S. PATENT DOCUMENTS 3,541,093 11/1970 Tull et al. ............................ 544/405
3,660,397 2/1972 Jones et al. ..................... 137/246.12

FOREIGN PATENT DOCUMENTS 1232758 5/1971 United Kingdom ................ 544/405

OTHER PUBLICATIONS

Ainsworth, et al., *Canadian J. Biochemistry*, vol. 56 (1978), pp. 457–461.
Adams, et al., *The Lancet* (Jan. 1976), pp. 186–188.
Olive, Peggy, *Cancer Research*, vol. 39, (Nov. 1979), pp. 4512–4515.
Anderson, et al. *British J. of Cancer*, vol. 37, (1978), pp. 103–106.

*Primary Examiner*—Mark L. Berch
*Assistant Examiner*—G. Hendricks
*Attorney, Agent, or Firm*—Thomas E. Arther; Mario A. Monaco

[57] ABSTRACT

N-Acyl derivatives of 6-(alkylamino)-5-chloro-3-nitropyrazinamines are disclosed to have activity in increasing the sensitivity of tumor cells to radiation. Also disclosed are methods of preparing such compounds and pharmaceutical compositions including such compounds.

12 Claims, No Drawings

N-ACYL DERIVATIVES OF 6-ALKYLAMINO 5-CHLORO-3-NITROPYRAZINAMINES FOR RADIATION THERAPY

BACKGROUND OF THE INVENTION

This application is a continuation-in-part of copending application Ser. No. 295,445 filed Aug. 24, 1981, now abandoned which in turn is a continuation-in-part of application Ser. No. 194,092 filed Oct. 6, 1980 and now abandoned.

This invention relates to N-acyl derivatives of 6-(alkylamino)-5-chloro-3-nitropyrazinamine used to sensitize tumor cells to therapeutic radiation and thus increase the effective therapeutic ratio of radiation treatment. It also relates to the process of preparing such compounds starting with 5,6-dichloro-3-nitropyrazinamine by first contacting said pyrazinamine with an acylating agent derived from a lower aliphatic carboxylic acid to afford the corresponding acylated pyrazinamine and further treating said acylated pyrazine with a lower (alkyl or substituted alkyl) amine compound to replace one of the chloro substituents and produce a 2-acylamino-6(alkylamino)-5-chloro-3-nitropyrazine. In addition, this invention relates to pharmaceutical compositions comprising such compounds and to methods of treatment comprising administering such compounds to patients undergoing radiation treatment to enhance the effectiveness of such treatment.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, but are believed to have a more favorable therapeutic ratio.

DETAILED DESCRIPTION OF THE INVENTION

The compositions of the present invention which are useful as radiation sensitizers are acylated derivatives of 6-(alkylamino)-5-chloro-3-nitropyrazinamines in combination with a pharmaceutical carrier.

A preferred group of such compounds is represented by the following structural formula:

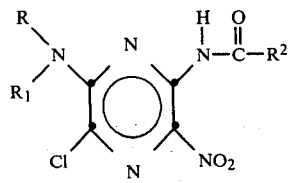

wherein R and $R^1$ are each hydrogen, $C_1$–$C_6$ loweralkyl and substituted lower alkyl having one or more amino $C_{1-6}$ loweralkylamino or dialkylamino, lower alkoxy, hydroxy or halo, including fluoro, chloro or bromo, $C_1$–$C_6$ lower alkenyl, and substituted lower alkenyl having one or more amino, $C_1$–$C_6$ alkylamino or dialkylamino, lower alkoxy, or hydroxy groups or when taken together and linked through an additional nitrogen or oxygen constitute a 5–7 member saturated heterocyclic ring comprising a morpholine, a piperazine or an N-substituted piperazine wherein the N-substituent is either hydrogen, $C_1$–$C_6$ alkyl, $C_1$–$C_6$ hydroxyalkyl, $C_1$–$C_6$ alkoxyalkyl;

and $R^2$ is a lower alkyl substituent;

and a pharmaceutical carrier.

One preferred subgroup of active compounds is represented by the formula:

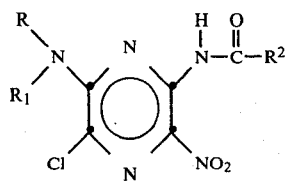

wherein

R is haloloweralkyl (fluoro, chloro or bromoalkyl) hydroxy loweralkyl and polyhydroxyloweralkyl of from 1–6 carbons, and $R^1$ is either hydrogen or is defined the same as R and $R^2$ is lower alkyl.

In accordance with the present invention the acylaminopyrazines described hereinabove are prepared by acylation and alkylation of the corresponding 5,6-dichloro-3-nitropyrazinamine. The starting material 5,6-dichloro-3-nitropyrazinamine is in turn prepared from the known 3-amino-5,6-dichloropyrazinecarboxylic acid, E. J. Cragoe, Jr., O. W. Woltersdorf, Jr., J. B. Bicking, S. F. Kwong and J. H. Jones, *J. Med. Chem.*, 10 66 (1967).

Thus in accordance with the process described in detail in Case 16550, U.S. application Ser. No. 194,100 of George D. Hartman, filed on Oct. 6, 1980, the 3-amino-5,6-dichloropyrazine carboxylic acid is heated with equal volumes of fuming sulfuric acid and fuming nitric acid to effect replacement of the carboxylic acid with a nitro group thus producing the 5,6-dichloro-3-nitropyrazinamine starting material.

The 5,6-dichloro-3-nitropyrazinamine is acylated by treatment with an acid halide or an acid anhydride of a loweraliphatic carboxylic acid. Preferably, the 5,6-dichloro-3-nitropyrazinamine is treated at room temperature with a large excess of an acid halide as for example, acetylchloride, acetyl bromide, propionyl chloride, butyryl chloride and the like in the presence of a base such as sodium bicarbonate. The reaction is preferably conducted by mixing the reactants without added solvent at room temperature and heating the reactants at reflux temperature of the mixture for a period of 5 hours to 4 days to insure maximum yield of product. Following the reaction period the entire mixture is evaporated in vacuo to remove excess acylating agents or alternatively quenched in water and extracted with a solvent for the product. After removal of volatile material by evaporation in vacuo the product remains as a residue and is conveniently further purified by chromatography over silica gel.

The 2-acylamino-5,6-dichloro-3-nitropyrazine thus produced is then treated with an amine compound to replace the chloro-substituent as illustrated hereinbelow;

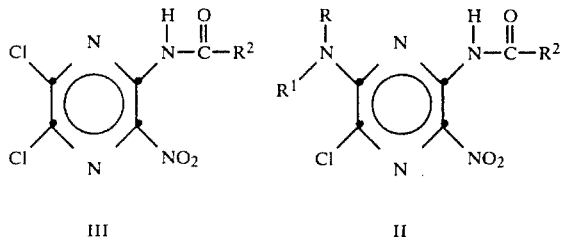

III    II

The reaction of the dichloroacylamino nitropyrazine III with the amine compound is preferably carried out in a solvent for the reactants. The solvent employed is a lower alkanol such as methanol, ethanol or isopropanol; ethers such as tetrahydrofuran; N,N-dialkylamides such as dimethyl formamide; and acetonitrile. The amine or thiol reagent is preferably present in approximately a 5–10% molar excess over the nitropyrazine. The reagents are first mixed and then preferably heated to a temperature of 20°–80° C. for a period of from 0.5 to 24 hours. In addition to the reagents and the solvent it is generally preferred to carry out the reaction in the presence of at least one equimolar amount of an organic base. Tertiary amines such as triethylamine and pyridine are preferred. The progress of the reaction is followed by the use of thin layer chromatography.

Following the reaction the product is recovered after first evaporating volatile solvents and reactants in vacuo leaving the product as a residue. This residue is then dissolved in a water immiscible solvent such as ethylacetate and the resulting extract of product washed with water and evaporated in vacuo to produce substantially pure product.

The method of treatment of human patients or domestic animals undergoing radiation treatment of malignant disease processes employs the compounds of the present invention in pharmaceutical compositions that are administered orally or parenterally, preferably intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface approximately equivalent to a dosage of 6 to 100 mg/kg of patient body weight as set forth in the "Nelson Textbook of Pediatrics" Eleventh Edition (1979), p. 31, Edited by Vaughan, McKay, Behrman, and Nelson.

The dosage range given is the effective dosage range and the decision as to the exact dosage used must be made by the administering physician based on his judgment of the patient's general physical condition. In determining the dose for the individual patient, the physician may begin with an initial dose of 0.25 gm/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs are preferred.

Capsules or tablets containing from 25, 50, 100 or 500 mg of drug/capsule or tablet are satisfactory for use in the method of treatment of our invention. For tablets or capsules the substantially pure compound may be combined with a pharmaceutically acceptable solid diluent or in the case of capsules filled directly into an appropriately sized capsule.

In the foregoing disclosure of applicant's invention, when reference is made to alkyl or alkoxy it is intended that loweralkyl or alkoxy are understood and the application is therefore limited to loweralkyl substituents containing from 1 to 6 carbon atoms and to loweralkoxy substituents containing from 1 to 6 carbon atoms.

The following examples are intended to illustrate but do not limt the process of preparation, product, compositions, or method of treatment aspects of the invention.

PREPARATION OF STARTING MATERIAL

Preparation of 5,6-dichloro-3-nitropyrazinamine (II)

To 450 ml concentrated sulfuric acid cooled to 10° is added 50.0 g (0.2 m) 3-amino-5,6-dichloropyrazine carboxylic acid. To this solution cooled to 0°–5°, is added a cold solution of 15 ml fuming sulfuric acid in 15 ml fuming nitric acid dropwise over 15 minutes. The reaction mixture is stirred at 0°–5° for 2 hours and then at ambient temperature for 2 hours. The reaction mixture is then poured onto ice and the yellow solid is collected. This solid is taken up in ethyl acetate, washed twice with saturated sodium carbonate solution and then the solution is filtered through a pad of silica gel. The resulting solution is evaporated in vacuo to afford 35 g of 5,6-dichloro-3-nitropyrazinamine, m.p. 169°–170° C.

EXAMPLE 1

N-[5-chloro-6(2,3-dihydroxypropyl)amino-3-nitropyrazinyl]acetamide

Step A: Preparation of N-(5,6-dichloro-3-nitropyrazin-2-yl)acetamide.

To 1.0 g of 5,6-dichloro-3-nitropyrazinamine in 15 ml acetyl chloride under nitrogen atmosphere at room temperature is added 0.84 g anhydrous sodium bicarbonate. The reaction mixture is then stirred and heated at reflux for 4 days. Excess acetyl chloride is then removed in vacuo and the residue is chromatographed on silica gel. The desired product is eluted from the column with chloroform.

Step B: N-[5-chloro-6(2,3-dihydroxypropyl)amino-3-nitropyrazinyl]acetamide.

To 0.20 g of acetamide in 35 ml isopropanol at room temperature is added 0.8 g triethylamine followed by 0.73 g 3-amino-1,2-propanediol. The reaction mixture is stirred at room temperature for 1 hour. Then, the solvent is removed in vacuo, and the residue taken up in ethyl acetate and washed twice with 10 ml water. The dried ethyl acetate extract is stripped in vacuo to give a yellow solid, which is recrystallized from acetonitrile to give the title compound, m.p. 130°–131°.

Employing the procedure substantially as described in Example 1, Step B but employing in Step B an equivalent amount of the indicated appropriate amine reagent there is produced.

| Example | Reagents | Product |
|---|---|---|
| 2 | 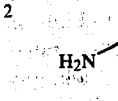 + 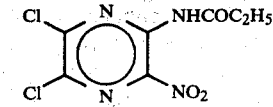 → | 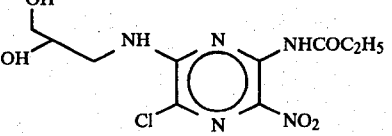<br>N—[5-Chloro-6-(2,3-dihydroxypropyl)amino-3-nitropyrazinyl]propionamide |
| 3 | 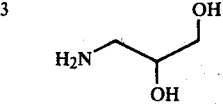 + 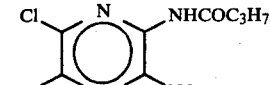 → | 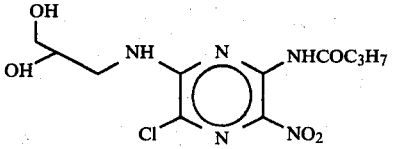<br>N—[5-Chloro-6(2,3-dihydroxypropyl)amino-3-nitropyrazinyl]butyramide |
| 4 | 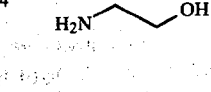 + 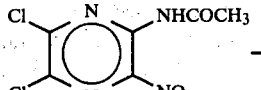 → | 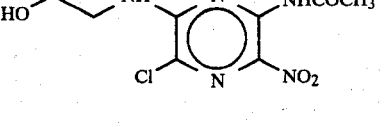<br>N—[5-Chloro-6(2-hydroxyethyl)amino-3-nitropyrazinyl]acetamide |
| 5 | 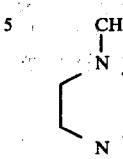 + 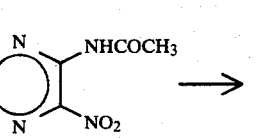 → | 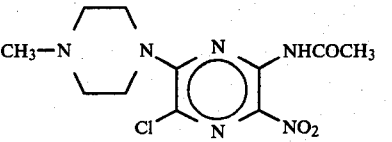<br>N—[5-chloro-6-(4-methyl-1-piperazinyl)-3-nitropyrazinyl]acetamide |
| 6 | 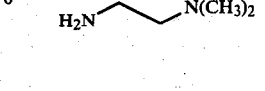 +  → | 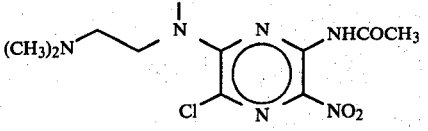<br>N—[5-Chloro-6(dimethlaminoethyl)-3-nitropyrazinyl]acetamide |

EXAMPLE 7

Tablet formulation

| Ingredients | Amount |
|---|---|
| Product of Example 1, 2, 3, 4, 5 or 6 | 25 mg |
| Calcium phosphate | 120 mg |
| Lactose | 50 mg |
| Starch | 23 mg |

-continued

| Ingredients | Amount |
|---|---|
| Magnesium Stearate | 1 mg |

EXAMPLE 8

Injectable Solution

| Ingredients | Amount |
| --- | --- |
| Product of Example 1, 2, 3, 4, 5 or 6 | 1 mg |
| Sodium Chloride | 9 mg |
| Distilled Water q.s. | 1 ml |

What is claimed is:

1. A pharmaceutical composition useful in enhancing the therapeutic effect of radiation treatment comprising an effective amount of a radiation enhancing compound of the formula:

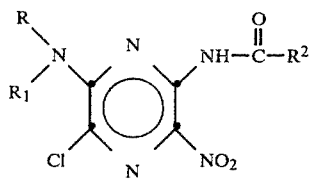

wherein R and $R^1$ are each hydrogen, $C_1$-$C_6$ loweralkyl and substituted lower alkyl having one or two amino $C_{1-6}$ loweralkylamino or dialkylamino, lower alkoxy, hydroxy or halo $C_1$-$C_6$ lower alkenyl, and substituted lower alkenyl having one or two amino, $C_1$-$C_6$ alkylamino or dialkylamino, lower alkoxy, or hydroxy groups or when taken together and linked through an additional nitrogen or oxygen constitute a 5–7 member saturated heterocyclic ring comprising a morpholine, a piperazine or an N-substituted piperazine wherein the N-substituent is either hydrogen, $C_1$-$C_6$ alkyl, $C_1$-$C_6$ hydroxyalkyl, $C_1$-$C_6$ alkyl, $C_1$-$C_6$ hydroxyalkyl, $C_1$-$C_6$ alkoxyalkyl; and $R^2$ is a lower alkyl substituent; and a pharmaceutical carrier.

2. A composition according to claim 1 wherein the radiation enhancing compound is N-[5-chloro-6-(2-hydroxyethyl)amino-3-nitropyrazinyl]acetamide.

3. A composition according to claim 1 wherein the radiation enhancing compound is N-[5-chloro-6(bis-2-hydroxyethyl)amino-3-nitropyrazinyl]acetamide.

4. A composition according to claim 1 wherein the radiation enhancing compound is N-[5-chloro-6(2,3-dihydroxypropyl)amino-3-nitropyrazinyl]acetamide.

5. A composition according to claim 1 wherein the radiation enhancing compound is N-[5-chloro-6(2,3-dihydroxypropyl)amino-3-nitropyrazinyl]propionamide.

6. A composition according to claim 1 wherein the radiation enhancing compound is N-[5-chloro-6(2,3-dihydroxypropyl)amino-3-nitropyrazinyl]butyramide.

7. A composition according to claim 1 wherein the radiation enhancing compound is N-[5-chloro-6-(4-methyl-1-piperazinyl)-3-nitropyrazinyl]acetamide.

8. A composition according to claim 1 wherein the radiation enhancing compound is N-[5-chloro-6-(dimethylaminoethyl)-3-nitropyrazinyl]acetamide.

9. A chloronitropyrazine compound of the formula:

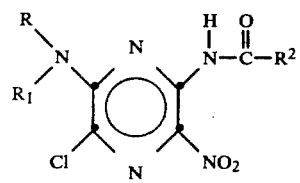

wherein

R is hydroxyloweralkyl, dihydroxyloweralkyl, or haloloweralkyl, and $R^1$ is hydrogen or R;

$R^2$ is a lower alkyl radical.

10. A chloronitropyrazine compound according to claim 9 which is N-[5-chloro-6(2,3-dihydroxypropyl)amino-3-nitropyrazinyl]acetamide.

11. A chloronitropyrazine compound according to claim 9 which is N-[5-chloro-6(2,3-dihydroxypropyl)amino-3-nitropyrazinyl]butyramide.

12. A method of enhancing the therapeutic effect of radiation treatment which comprises administering to a patient in need of such radiation treatment an effective sensitizing amount of a compound of the formula:

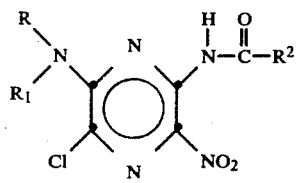

wherein R, $R^1$ and $R^2$ are defined as in claim 1.

* * * * *